(12) United States Patent
Rapp et al.

(10) Patent No.: US 8,293,084 B2
(45) Date of Patent: Oct. 23, 2012

(54) METHOD FOR AUTOMATED HIGH THROUGHPUT IDENTIFICATION OF CARBOHYDRATES AND CARBOHYDRATE MIXTURE COMPOSITION PATTERNS AS WELL AS SYSTEMS THEREFORE

(75) Inventors: Erdmann Rapp, Magdeburg (DE); Jana Schwarzer, Magdeburg (DE); Udo Reichl, Magdeburg (DE); Christian Bohne, Magdeburg (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 354 days.

(21) Appl. No.: 12/428,003

(22) Filed: Apr. 22, 2009

(65) Prior Publication Data

US 2009/0288951 A1   Nov. 26, 2009

Related U.S. Application Data

(60) Provisional application No. 61/047,156, filed on Apr. 23, 2008.

(51) Int. Cl.
*G01N 27/447* (2006.01)
(52) U.S. Cl. ........... 204/455; 702/32; 436/139; 700/273
(58) Field of Classification Search .................. 204/455, 204/452, 603, 605; 702/27, 28, 32; 436/8, 436/52, 139; 700/273
See application file for complete search history.

(56) References Cited

OTHER PUBLICATIONS

Khandurina, J., et al., "Large-scale carbohydrate analysis by capillary array electrophoresis: Part 2. Data normalization and quantification", Electrophoresis, vol. 25, 2004, p. 3122-3127.*
Callewaert, N., et al., "Ultrasensitive profiling and sequencing of N-linked oligosaccharids using standard DNA-sequencing equipment", Glycobiology, vol. 11, No. 4, Apr. 2001, p. 275-281.*

* cited by examiner

*Primary Examiner* — J. Christopher Ball
(74) *Attorney, Agent, or Firm* — Whitham Curtis Christofferson & Cook, PC

(57) ABSTRACT

The present invention relates to methods for the identification of compounds in carbohydrate mixture compositions as well as the determination of carbohydrate mixture composition patterns, based on e.g. orthogonal cross determining migration time (indices) using capillary gel electrophoresis-laser induced fluorescence and identifying said carbohydrate components based on comparing said migration time (indices) with standard migration time (indices) from a database which data are preferably also orthogonal cross determined. In a further aspect, the present invention relates to a method for carbohydrate mixture composition pattern profiling, like glycosylation pattern profiling using capillary gel electrophoresis-laser induced fluorescence (CGE-LIF). In another aspect, the present invention refers to a system for an automated determination and/or identification of carbohydrates and/or carbohydrate mixture composition patterns (e.g.: glycosylation patterns). Finally, the present invention relates to a database containing e.g. orthogonal cross normalized migration times and/or migration time indices of carbohydrates.

20 Claims, 5 Drawing Sheets

| $t_{mig}$ IgG N-glycane (DP) | $t_{mig}$ IgG N-glycane (bp) |
|---|---|
| 5767 | 59 |
| 8352 | 174 |
| 8429 | 177.5 |
| 8927 | 200 |
| 9203 | 212 |
| 9248 | 214 |
| 9584 | 229 |
| 9705 | 234.5 |
| 9827 | 240 |
| 9869 | 241.8 |
| 9880 | 242.3 |
| 10359 | 264 |
| 10573 | 273 |

US 8,293,084 B2

METHOD FOR AUTOMATED HIGH THROUGHPUT IDENTIFICATION OF CARBOHYDRATES AND CARBOHYDRATE MIXTURE COMPOSITION PATTERNS AS WELL AS SYSTEMS THEREFORE

CROSS-REFERENCE TO RELATED APPLICATIONS

This application claims priority to U.S. Provisional Patent Application 61/047,156 filed Apr. 23, 2008.

The present invention relates to methods for identification of carbohydrates compositions, e.g. out of complex carbohydrate mixtures, as well as the determination of carbohydrate mixture composition patterns (e.g.: of glycosylation patterns) based on e.g. orthogonal cross determining migration time indices using capillary gel electrophoresis-laser induced fluorescence and identifying said carbohydrate components based on comparing said migration time indices with standard migration time indices from a database which data are preferably also orthogonal cross determined. In a further aspect, the present invention relates to a method for carbohydrate mixture composition pattern profiling (e.g.: for glycosylation pattern profiling) using capillary gel electrophoresis-laser induced fluorescence (CGE-LIF) generating electropherograms from said mixtures. In another aspect, the present invention refers to a system for an automated determination and/or identification of carbohydrates and/or carbohydrate mixture composition patterns, (e.g.: glycosylation patterns). Finally, the present invention relates to a software package for data-processing and result-visualization, having an integrated database containing e.g. orthogonal cross normalized migration times of carbohydrates.

BACKGROUND OF THE INVENTION

The importance of glycosylation in many biological processes is commonly accepted and has been discussed in detail throughout the literature over the last 30 years. Glycosylation is a common and highly diverse post-translational modification of proteins in eukaryotic cells. Various cellular processes have been described, involving carbohydrates on the protein surface. The importance of glycans in protein stability, protein folding and protease resistance have been demonstrated in the literature. In addition, the role of glycans in cellular signalling, regulation and developmental processes has been demonstrated in the art.

The oligosaccharides are mainly attached to the protein backbone, either by N-(via Asn) or O-(via Ser-Thr) glycosidic bonds, whereas N-glycosylation represents the more common type found in glycoproteins. Variations in glycosylation site occupancy (macroheterogeneity), as well as variations in these complex sugar residues attached to one glycosylation site (microheterogeneity) result in a set of different protein glycoforms. These have different physical and biochemical properties, which results in additional functional diversity. In manufacturing of therapeutic proteins in mammalian cell cultures, macro- and microheterogeneity were shown to affect properties like protein solubility, structural stability, protease resistance, or biological and clinical activity, see for example Butler, M., Cytotechnology, 2006, 50, 57-76. For instance, the relevance of the glycosylation profile for the therapeutic profile of monoclonal antibodies is well documented; see e.g. Parekh, et al., Nature, 1985, 316, 452-457.

Glycan biosynthesis is a non-template-driven process, involving the cell glycosylation machinery. N-glycan structures are also depending on various factors during the production process, like substrates levels and other culture conditions. Thus, the glycoprotein manufacturing does not only depend on the glycosylation machinery of the host cell but also on external parameters, like cultivation conditions and the extracellular environment. Culture parameters affecting glycosylation include temperature, pH, aeration, supply of substrates or accumulation of byproducts such as ammonia and lactate. In case of recombinant glycoprotein or antibody manufacturing, characterization of glycosylation profiles attracts increasing interest. In particular, because of regulatory reasons, the glycosylation profile of drugs has to be determined.

Today, complex soluble but also oligomeric and/or polymeric carbohydrate mixtures, obtained synthetically or from natural sources, like plants or human or animal milk are used as nutrition additives or in pharmaceuticals. The occurrence of sialic acids or sialic acid derivatives and the occurrence of monosaccharides having a phosphate, sulphate or carboxyl group within those complex natural carbohydrates is even increasing their complexity. Because of this complexity, those prebiotic oligo- or polysaccharides, like neutral or acidic galacto-oligosaccharides, long chain fructo-oligosaccharides, which can have nutritional and/or biological effects, are gaining increasing interest for food and pharmaceutic industry.

A wide range of strategies and analytical techniques for analysing glycoproteins, glycopeptides and released N-glycans or O-glycans have been established including e. g 2D-HPLC profiling, mass spectrometry and lectin affinity chromatography, as reviewed by Geyer and Geyer, Biochimica Et Biophysica Acta-Proteins and Proteomics 2006, 1764, 1853-1869 and Domann et al., Practical Proteomics, 2007, 2, 70-76.

To obtain structural data of complex molecules, today carbohydrates are either analysed by mass spectrometry (MS) or nuclear magnetic resonance spectroscopy (NMR) which are generally laborious and time consuming techniques regarding sample preparation and data interpretation.

Each of these techniques has advantages as well as drawbacks. Choosing one, respectively a set of these methods for a given problem can become a time- and labor-intensive task. For example, NMR provides detailed structural information, but is a relatively insensitive method (nmol), which can not be used as a high-throughput method. Using MS is more sensitive (fmol) than NMR. However, quantification can be difficult and only unspecific structural information can be obtained without addressing linkages of monomeric sugar compounds. Both techniques require extensive sample preparation and also fractionation of complex glycan mixtures before analysis to allow evaluation of the corresponding spectra. Furthermore, a staff of highly skilled scientists is required to ensure that these two techniques can be performed properly.

Although separation techniques based on the capillary electrophoresis principle, like capillary gel electrophoresis where considered for complex carbohydrate separation in the art before, e.g Callewaert, N. et al, Glycobiology 2001, 11, 275-281, WO 01/92890, Callewaert, N. et al, Nat Med. 2004, 10 429-434, there is still an ongoing need for a reliable and fast system allowing automated high throughput carbohydrate analysis.

As identified by Domann et al, normal phase chromatography and capillary gel electrophoresis have an excellent selectivity for the analysis of fluorescently labelled glycans. Serious drawbacks regarding the limit of detection and the linear dynamic range of CGE-LIF compared to normal phase liquid chromatography with fluorescence detection have been reported. Furthermore with respect to CGE-LIF no methods are described in the art allowing to rapidly monitor alterations in carbohydrate mixture composition patterns (e.g. glycosylation patterns) including fast and straightforward structure elucidation, without the need for complex data evaluation. Further, there is a need in the art to provide means and methods allowing for determination and identification of carbohydrate mixtures of unknown composition enabling identification of the carbohydrate structures. In particular, there is a need for a sensitive but reproducible and robust system and method allowing the identification or determination of carbohydrate mixture composition patterns (e.g.: glycosylation patterns) as well as of carbohydrate compositions of unknown constitution in automated high throughput mode. In particular, for the latter, the method and system must ensure very accurate and reproducible analysis of carbohydrates whereby said analysis is essentially independent from sample type and origin, timepoint of analysis, laboratory, instrument and operator.

DETAILED DESCRIPTION OF THE PRESENT INVENTION

Figure 1:
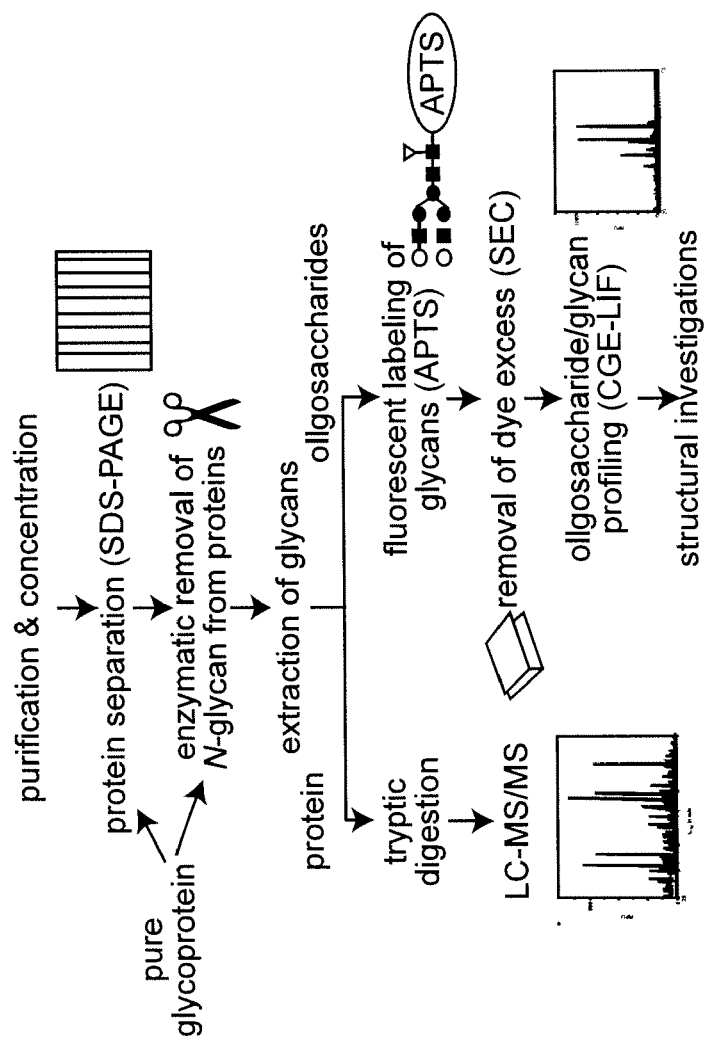
FIG. 1 provides a workflow of the carbohydrate analysis according to the present invention (right side) and of the prior art (left side).
Figure 2:
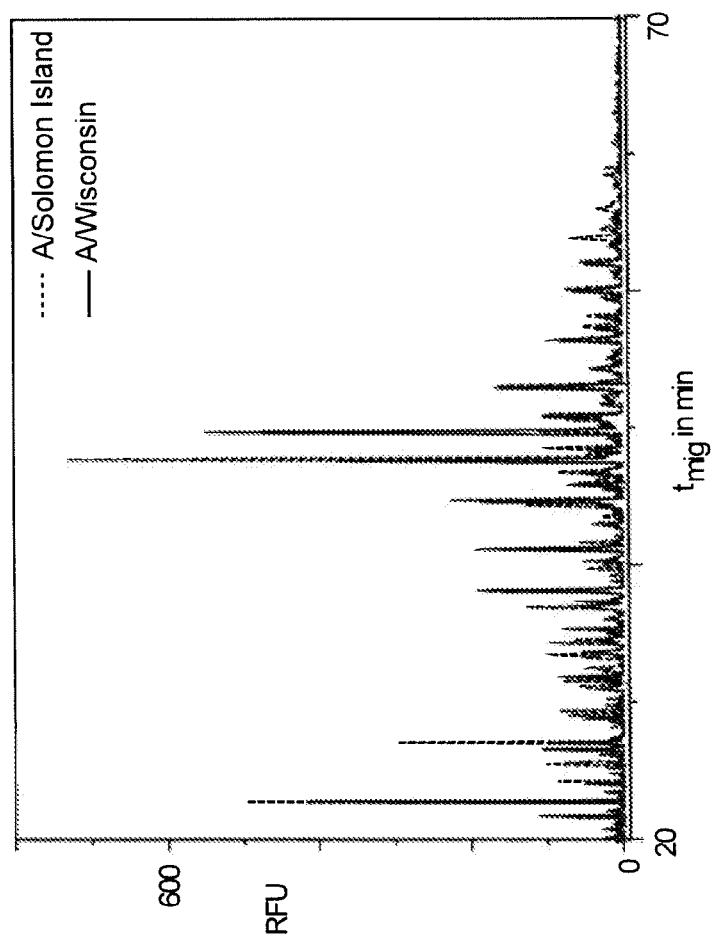
FIG. 2 provides a fingerprint comparison of glycan pools of the membrane glycoprotein "hemagglutinin" of two different influenza virus strains.
Figure 3:
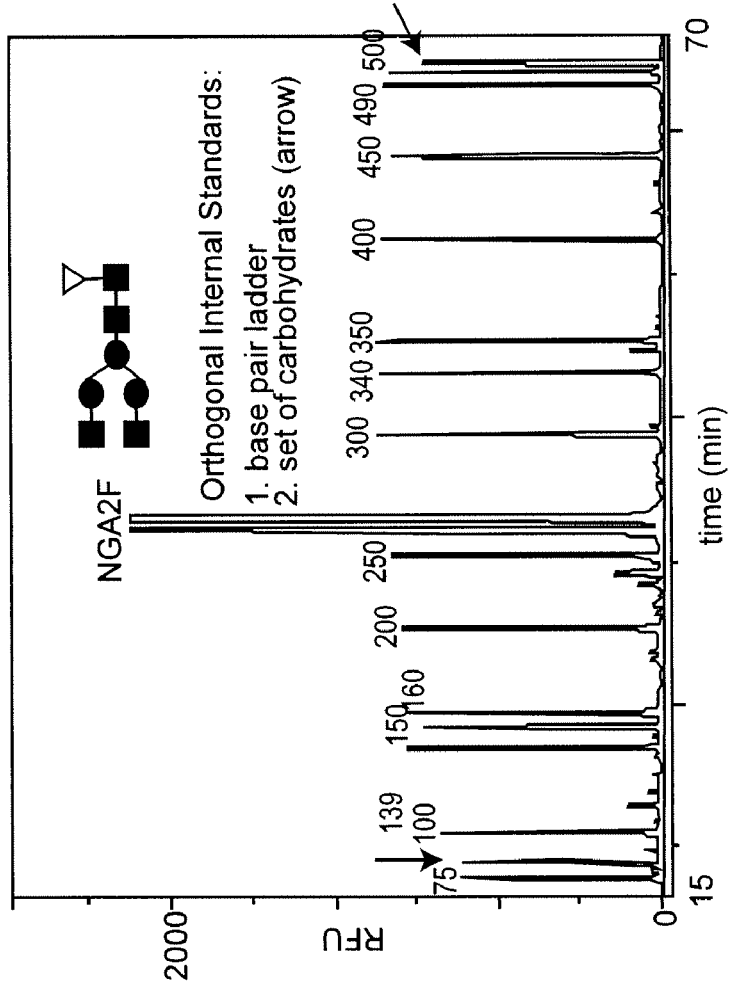
FIG. 3 shows the orthogonal cross standardization of migration times using two orthogonal internal standards, double normalizing migration times to internal standard indices. First standard: DNA base pair ladder, sizes are given in the table, second standard: set of carbohydrates (arrows) located outside the range of presence of compounds to be analyzed.
Figures 4, 5:
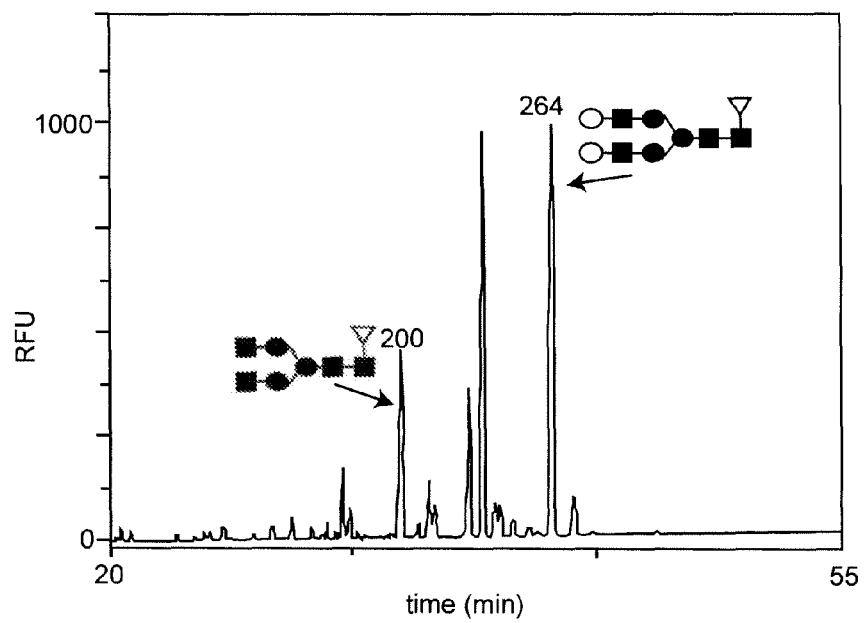
FIG. 4 shows the standardization of the migration indices calculated as "bp-indices".
FIG. 5 shows an analysis of an unknown carbohydrate composition obtained from glycans together with the identification of carbohydrate components based on the bp-index matching using the database according to the present invention.

In a first aspect, the present invention relates to a method for an automated determination and/or identification of carbohydrates and/or a carbohydrate mixture composition pattern profiling (e.g.: glycosylation pattern profiling) comprising the steps of:
a) obtaining a sample containing at least one carbohydrate;
b) labelling said carbohydrate(s) with a fluorescent label;
c) providing standard(s) of known composition;
d) determining the migration time(s) of said carbohydrate(s) and of the standard(s) of a known composition using capillary gel electrophoresis-laser induced fluorescence;
e) normalizing the migration time(s) of step d) to indices based on given standard migration time indice(s) of the standard(s);
(f) comparing the migration time indice(s) of the carbohydrate(s) with standard migration time indice(s) from a database;
g) identifying or determining the carbohydrate(s) and/or the carbohydrate mixture composition patterns.

In a preferred embodiment, the migration time(s) of step d) are orthogonal cross normalized using two different standards.

In the following the term "carbohydrate(s)" refers to monosaccharide(s), like glucose, galactose, mannose, fructose, fucose, N-acetylglucoseamine, sialic acid; disaccharide(s), like lactose, sucrose, maltose, cellobiose; oligosaccharide(s), like N-glycans, O-glycans, galactooligosaccharides, fructooligosaccharides; and polysaccharide(s), like amylase, amylopektin, cellulose, glycogen, glycosaminoglycan, or chitin.

The term "glycoconjugate(s)" as used herein means compound(s) containing a carbohydrate moiety, examples for glycoconjugates are glycoproteins, glycopeptides, proteoglycans, peptidoglycans, glycolipids, GPI-anchors, lipopolysaccharides.

The term "carbohydrate mixture composition pattern profiling" as used in means establishing a pattern specific for the examined carbohydrate mixture composition based on the number of different carbohydrates present in the mixture, the relative amount of said carbohydrates present in the mixture and the type of carbohydrate present in the mixture and profiling said pattern e.g. in a diagram or in a graphic, e.g. as an electropherogram. Thus, fingerprints illustrated e.g. in form of an electropherogram, a graphic, or a diagram are obtained. For example glycosylation pattern profiling based on fingerprints fall into the scope of said term. In this connection, the term "fingerprint" as used herein refers to electropherograms being specific for a carbohydrate or carbohydrate mixture, a diagram or a graphic.

The term "quantitative determination" or "quantitative analysis" refers to the relative and/or absolute quantification of the carbohydrates. Relative quantification can be done straight foreward via the individual peak heights of each compound, which corresponds linear (within the linear dynamic range of the LIF-detector) to its concentration. The relative quantification outlines the ratio of each of one carbohydrate compound to another carbohydrate compound(s) present in the composition or the standard. Further, absolute (semi-)quantitative analysis is possible.

The term "orthogonal cross normalization" resp., "orthogonal cross standardization" of migration times refer to double normalization of migration times by two sets of completely different (orthogonal) internal standards. Said orthogonal internal standdards of known composition, e.g. can be a standard DNA base pair ladder (fluorescently labelled with a different tag than the carbohydrate samples) and a pair of carbohydrates (e.g. mono-, di-, tri-, tetra- and/or pentamer and a 20mer or higher) fluorescently labelled with the same tag than the carbohydrate samples, but eluting/mibrating out of range of the fingerprint of the carbohydrate samples to be analysed.

The present inventors found that using capillary gel electrophoresis with laser induced fluorescence (CGE-LIF) allows a fast but robust and reliable analysis and identification of carbohydrates and/or carbohydrate mixture composition patterns (e.g.: glycosylation patterns of glycoproteins). The methods according to the present invention used in the context of glycoprotein analysis allow to visualize carbohydrate-mixture compositions (e.g.: glycan-pools of glycoproteins) including structural analysis of the carbohydrates while omitting highly expensive and complex equipment, like mass spectrometers or NMR-instruments. Due to its superior separation performance and efficiency compared to other separation techniques, capillary electrophoresis techniques, in particular, capillary gel electrophoresis are considered for complex carbohydrate separation before but said technique was not recommended in the art due to drawbacks which should allegedly provided when using said method, see e. g. Domann et al. or WO2006/114663. However, when applying the method according to the present invention, the technique of CGE-LIF allows for sensitive and reliable determination and identification of carbohydrate structures. In particular, the use of a capillary DNA-sequencer, (e. g. 4-Capillary Sequencers: 3100-Avant Genetic Analyzer and 3130 Genetic Analyzer; 16-Capillary Sequencer: 3100 Genetic Analyzer and 3130xl Genetic Analyzer; 48-Capillary Sequencer: 3730 DNA Analyzer; 96-Capillary Sequencer: 3730xl DNA Analyzer from Applied Biosystems) allows the performance of the method according to the present invention. The advanced method of the invention enables the characterization of variations in complex composed natural or synthetic carbohydrate mixtures and the characterization of carbohydrate mixture composition patterns (e.g.: protein glycosylation patterns), directly by carbohydrate "fingerprint" alignment in case of comparing sampled with known carbohydrate mixture compositions.

The method according to the present invention is a relatively simple and robust but nevertheless highly sensitive and reproducible analysis method with high separation performance.

Especially the combination of the above mentioned instruments with up to 96 capillaries in parallel and the software/database tool enclosed within the invention, enables an automated high throughput analysis.

In another aspect, the present invention relates to a method for an automated carbohydrate mixture composition pattern profiling comprising the steps of:
a) providing a sample containing a carbohydrate mixture composition;
b) labelling of said carbohydrate mixture composition with a fluorescent label;
c) providing a second sample having a known carbohydrate mixture composition pattern to be compared with;
d) generating electropherogramms (fingerprints) of the carbohydrate mixture compositions of the first and second sample using capillary gel electrophoresis-laser induced fluorescence;
e) comparing the obtained electropherogramms (fingerprints) of the first sample and the second sample;
f) analyzing the identity and/or differences between the electropherogramms (fingerprints) of the first and the second sample.

As shown in FIG. 1 outlining a workflow of carbohydrate analysis, after processing of samples, electropherograms—"fingerprints"—are generated and, according to the method of the present invention, simple and straightforward structural investigation and identification of carbohydrates of a test sample (e.g. glycan pool of glycoproteins) via automatic matching their normalized CGE migration times (migration time indices) with normalized CGE migration times of carbohydrates with known structures derived from a database whereby said normalized CGE migration times are preferably orthogonal cross normalized CGE migration times, is possible.

The database which is an essential element of the present invention, also referred to as "fingerprint library", contains structural information of known carbohydrates having assigned specific normalized migration time indices, namely CGE migration times. This database allows automated, fast and straightforward structural identification of carbohydrates from natural and recombinant glycoproteins after processing or any other sample containing mono-, oligo-, or polysaccharides by simple assignment of peaks from fingerprints to carbohydrates with known structures. This can be done fully automated via migration time matching of test samples with e g. orthogonal cross normalized migration times (migration time indices) of carbohydrates from corresponding database in a high throughput mode using a CGE-LIF system with e.g. up to 96 capillaries or more in parallel.

In a preferred embodiment, the test sample contains a mixture of carbohydrates. Preferably, said carbohydrates to be identified or determined are oligosaccharides. For example, said oligosaccharides/glycans are obtained from processing of glycoproteins, as e g. shown in FIG. 1. That is, the sample represents an extraction of glycans and the method according to the present invention allows for the identification of a glycosylation pattern profile.

The invention is based on separating and detecting said carbohydrate mixtures (e.g.: glycan pools) utilizing the CGE-LIF technique, e.g. using a capillary DNA-sequencer which enables generation of carbohydrate composition pattern fingerprints, the automatic structure analysis of the separated carbohydrates via database matching of the preferably orthogonal cross normalized CGE-migration time of each single compound of the test sample mixture. The method claimed herein allows carbohydrate mixture composition profiling of synthetic or natural sources, like glycosylation pattern profiling of glycoproteins. The normalization of the migration times of the carbohydrates to migration time indices is based on the usage of a standard of known composition. In case of orthogonal cross normalization, two different standards of known composition and size are used. In particular, a first standard of known composition is preferably a standard base pair ladder conventionally used in a DNA-sequencer. The use of said standard base pair ladder allows to normalize each run of the DNA sequencer. Thus, an individual bp-index for each of the carbohydrate molecules is obtained. In case of the preferred embodiment of orthogonal cross normalization, as a second orthogonal internal standard, a set of fluorescently labelled carbohydrates which elute/migrate out of range of the fingerprint of the samples to be analyzed. This set (two or more) of flourescently labelled carbohydrates, e.g. can be labelled carbohydrates mono-, di-, tri-, tetra-, and/or pentamer and a labelled carbohydrates 20-mer (or higher). The monomer elutes in front of the sample molecules while the oligomer(e.g. 20mer) is big enough to elute after the last sample peat. This second internal standard can be used for the precise adjustment of the calibration curve, regading y-axis intercept and slope.

This orthogonal cross determination of migration time indices allows an extremely exact and absolute reproducilbe CGE-LIF analysis of carbohydrates, independent form sample type and origin, timepoint of analysis, laboratory, instrument and operator.

The use of said method in combination with the system also allows to analyze said carbohydrate mixture compositions quantitatively. Thus, the method according to the present invention as well as the system represents a powerful tool for monitoring variations in the carbohydrate mixture composition like the glycosylation pattern of proteins without requiring complex structural investigations. For fluorescently labelled carbohydrates, the LIF-detection allows a limit of detection down to the attomolar range.

The standard necessary for normalization of each run may be present in a separate sample or may be contained in the carbohydrate sample to be analysed. Preferably, the standard (s) necessary are contained in each single carbohydrate sample to be analysed.

The fluorescent label used for labelling the carbohydrates may be e.g. the fluorescent labels 8-amino-1,3,6-pyrenetrisulfonic acid also referred to as 9-aminopyrene-1,4,6-trisulfonic acid (APTS), 8-aminonaphtalene-1,3,6-trisulfonic acid (ANTS) or other preferably multiple charged fluorescent dyes.

Based on the presence of the standard, preferably orthogonal standards, qualitative and quantitative analysis can be effected. Relative quantification can be done easily just via the individual peak heights of each compound, which corresponds linear (within the linear dynamic range of the LIF-detector) to its concentration.

The present invention resolves drawbacks of other methods known in carbohydrate analysis, like chromatography, mass spectrometry and NMR. NMR and mass spectrometry represent methods which are time and labour consuming technologies.

In addition, expensive instruments are required to conduct said methods. Further, most of said methods are not able to be scaled up to high troughput methods, like NMR techniques. Using mass spectrometry allows a high sensitivity. However, configuration can be difficult and only unspecific structural information could be obtained with addressing linkages of monomeric sugar compounds. HPLC is also quite sensitive depending on the detector and allows quantification as well. But as mentioned above, real high throughput analyses are only possible with an expensive massive employment of HPLC-Systems and solvents.

Other techniques known in the art are based on enzymatic treatment which can be very sensitive and result in detailed structure information, but require a combination with other methods like HPLC, MS and NMR. Further techniques known in the art relates to lectin or monoclonal antibody affinity providing only preliminary data without given definitive structural information.

The methods according to the present invention allow for high-throughput identification of carbohydrates mixtures having unknown composition or for high-throughput identification or profiling of carbohydrate mixture composition patterns (e,g.: glycosylation patterns of glycoproteins). In particular, the present invention allows determining the components of the carbohydrate mixture composition quantitatively.

The method of the present invention enables the fast and reliable measurement even of complex mixture compositions, and therefore enables determining and/or identifying the carbohydrates and/or carbohydrate mixture composition patterns (e.g.: glycosylation pattern) independent of the apparatus used but relates to the preferably orthogonal cross normalized migration times (migration time indices) only.

The invention allows for application in diverse fields. For example, the method maybe used for analysing the glycosylation of mammalian cell culture derived molecules, e.g. recombinant proteins, antibodies or virus or virus components, e.g. influenza A virus glycoproteins. Information on glycosylation patterns of said compounds are of particular importance for food and pharmaceuticals. Starting with the separation of complex protein mixtures by 1D/2D-gel-electrophoresis, the method of the present invention could be used also for glycan analysis of any other glycoconjugates. Moreover, pre-purified glycoproteins, e.g by chromatography or affinity capturing, can be handled as well as by the method according to the present invention, substituting the gel separation and in-gel-degylcosylation step with in-solution-deglycosylation, continuing after protein and enzyme precipitation. Finally, complex soluble oligomeric and/or polymeric saccharide mixtures, obtain synthetically or from natural sources which are nowadays important nutrition additives/surrogates or as used in or as pharmaceuticals can be analysed.

Thus, two types of analyses may be performed on the carbohydrate mixtures. On the one hand, carbohydrate mixture composition pattern profiling like glycosylation pattern profiling may be performed and, on the other hand, carbohydrate identification based on matching carbohydrate migration time indices with data from a database is possible.

Therefore, a wide range of potential applications for the method according to the present invention is given ranging form production and/or quality control to early diagnosis of diseases which are producing, are causing or are caused by changes in the glycosylation patterns of glycoproteins.

In particular, in medical diagnosis, e.g. chronic inflammation recognition or early cancer diagnostics, where changes in the glycosylation patterns of proteins are strong indicators for disease, the method may be applied. The variations in the glycosylation pattern could simply be identified by comparing the obtained fingerprints regarding peak numbers, heights and migration times. Thus, disease markers may be identified, as it is described in similar proteomic approaches. It is, similar to comparing the proteomes of an individual at consecutive time points, the glycome of individuals could be analysed as indicator for disease or identification of risk patients.

Further, the method allows the differentiation of recombinant compounds vis-a-vis with natural compounds. For example, said method may be used in doping tests.

Another embodiment of the present invention relates to systems for determining and/or identifying carbohydrate mixture composition patterns, like glycosylation pattern profiling comprising a capillary gel electrophoresis-laser induced fluorescence apparatus; a data processing unit comprising memory containing a database; and an output unit.

Figure 6:
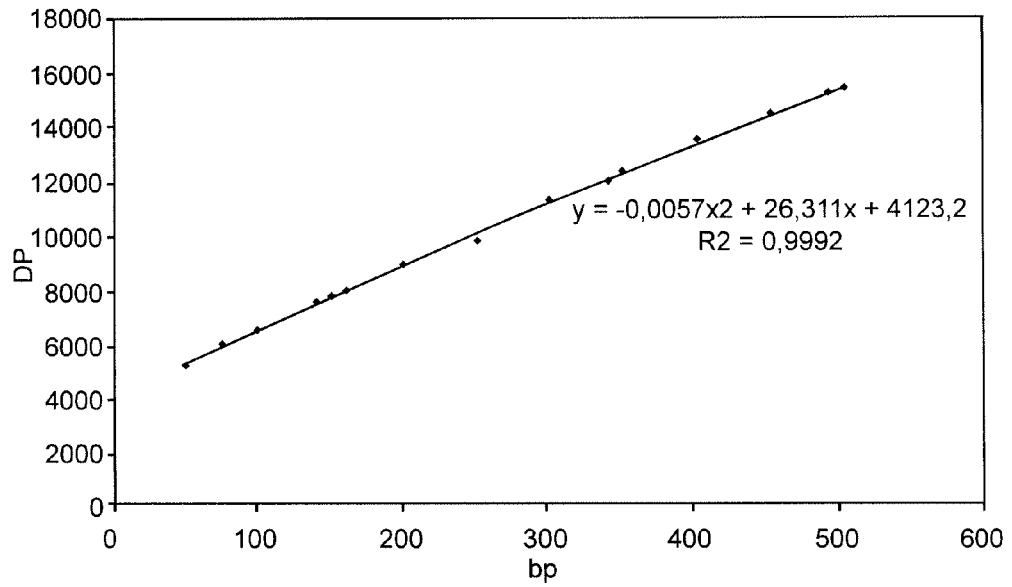
FIG. 6 shows the polynomial-fit of internal standard peaks.
Figure 7:
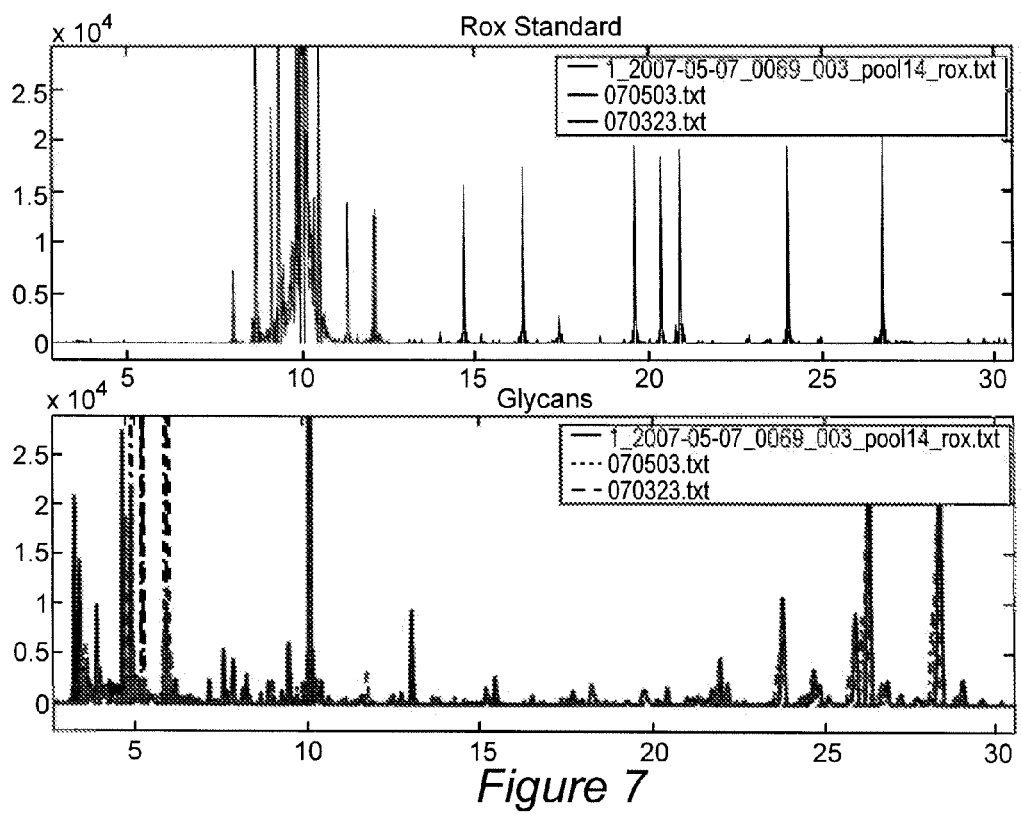
FIG. 7 provides an overlay of sample electropherograms from several runs, adjusted to each other via polynomial-fit.

Preferably, the capillary gel electrophoresis-laser induced fluorescence apparatus is a capillary DNA sequencer. The database contains the normalized migration times (migration time indices, e.g. given as base pair indices), preferably, orthogonal cross normalized migration times. In the data processing unit raw data from the CGE-LIF-apparatus, like the capillary DNA sequencer (sample trace and internal standard ladder trace) are extracted, e.g. extracted in ASCII-format and filed on variables. The peaks within the electropherogram of the internal standard of each sample are identified. For direct comparison of different runs, the internal standard peaks from the different runs are adjusted to each other via polynomial-fit, see also FIG. 6. The sample electropherograms are orhtogonal cross normalized to the adjusted time scale of its two orthogonal internal standards, each with its previously determined individual polynomial-fit and precise readjustment of the calibration curve, regarding the y-axis intercept and slope, and, therefore, they can be compared directly via simple overlay, see also FIG. 7, showing an overlay of sample electropherograms from several runs adjusted to each other via polynomial-fit.

This means, each measured sample electropherogram, which always runs together with the internal standard, for example, the internal standard base pair ladder, is translated/formatted by an algorithm from migration time to internal standard index and therefore normalized and indexed. Preferably, the standard is an orthogonal internal standards of the internal base pair ladder and a pair of known carbohydrates laying outside in size of the range of the carbohydrates to be analyzed (e.g. one monomer and one large oligomer) whereby said standard carbohydrates are preferably labelled with the same label as the carbohydrates to be analyzed, thus, allowing orthogonal cross normalization. The processed and normalized data enable direct comparison of different runs and allow the identification or exclusion of carbohydrates structures by simple migration time index matching of carbohydrates peaks from the sample with those already deposited within the data base. The invention enables the qualitative and quantitative analysis and the direct comparison of test carbohydrates samples, independent from the operator, instrument or laboratory, in particular, in case of orthogonal cross normalization.

Thus, another aspect of the present invention relates to the data base containing normalized migration times (indices) of carbohydrates, said migration time indices are based on CGE-LIF-measurement and are obtained by
  a) analysing known carbohydrate structures in a sample together with an internal standard at the same time with a capillary gel electrophoresis-laser induced fluorescence means;
  b) determining the migration time of said carbohydrate compound(s) and the standard;
  c) normalizing the migration times of step b) based on given standard migration time(s) of the internal standard;
  d) assigning the normalized carbohydrate compound migration times to standard migration time indices.

Preferably, the above database contains orthogonal cross normalized migration times using at least two different standards.

The home built data base Is integrated e.g. into the home built software tool and can be fitted by the user himself. Said data base may be provided as an external tool or may be provided from a centralized server.

The structure data base/library with the assigned normalized CGE-migration times, e.g. base pairs indices, is generated by measuring single carbohydrates of known structure. The general library/data base where the known carbohydrate structures are deposited together with their migration time indices, enable sample and system independent data base matching of carbohydrate mixture composition patterns (fingerprints) like glycan pools from test samples. Preferably, said normalized CGE-migration times are orthogonal cross normalized CGE-migration times.

The data from the CGE-LIF are extracted in computer readable form and filed on variables. The peaks within the electropherogram of the internal standard(s) of each sample are identified and annotated. The time scales of the sample electropherograms are normalized and transferred from time to the internal standard domain, e.g. the base pair annotation, each to its corresponding internal standard trace, each with its previously determined individual polynomial-fit and in case of orthogonal standards and precies readjustment, and, therefore, the compound peaks are normalized, preferably orthogonal cross normalized.

The data from the data base of carbohydrate standards of known structures allow to identify unknown compounds with identical, preferably orthogonal cross, normalized migration times, just via matching their migration time indices with those from the library.

The invention claimed is:
1. A method for an automated determination and/or identification of carbohydrates and/or carbohydrate mixture composition pattern profiling comprising the steps of:
  a) obtaining a sample containing one or more carbohydrate(s);
  b) labeling said one or more carbohydrate(s) with a fluorescent label;
  c) adding at least one standard of known composition to the sample containing the one or more carbohydrate(s);
  d) determining migration time(s) of said one or more carbohydrate(s) and the standard of known composition using capillary gel electrophoresis-laser induced fluorescence;
  e) normalizing the migration time(s) to migration time indice(s) based on given standard migration time indice(s) of the standard;
  f) comparing said migration time indice(s) of the one or more carbohydrate(s) with standard migration time indice(s) from a database; and
  g) identifying or determining the one or more carbohydrate(s) and/or carbohydrate mixture composition patterns, whereby at least two orthogonal standards are added in step c) and orthogonal cross normalization is performed in step e) based on the given standard migration time indices of the at least two orthogonal standards.

2. The method according to claim 1, wherein the sample contains a mixture of carbohydrates.

3. The method according to claim 1, wherein the sample is an extraction of glycans and the method allows for the identification of a glycosylation pattern profile.

4. The method according to claim 3, wherein the glycosylation pattern of a glycoprotein is identified.

5. The method according to claim 1, wherein the standard of known composition is a standard base pair ladder.

6. The method according to claim 1 wherein the at least two orthogonal standards include a standard base pair ladder and a set of mono- and oligosacchardies.

7. The method according to claim 1, wherein the fluorescent label is 8-amino-1,3,6-pyrenetrisulfonic acid.

8. A method for an automated carbohydrate mixture composition pattern profiling comprising the steps of:
  a) providing a first sample containing a carbohydrate mixture composition;
  b) labeling of said carbohydrate mixture composition with a fluorescent label;
  c) adding a second sample having a known carbohydrate mixture composition pattern to said first sample;
  d) generating electropherograms of the carbohydrate mixture composition of the first and second sample using capillary gel electrophoresis-laser induced fluorescence;
  e) comparing an electropherogram generated in step d) or the migration times calculated therefrom of the first sample and the second sample;
  f) analysing the identity and/or differences between the carbohydrate mixture composition pattern profiles of the first and the second sample.

9. The method according to claim 8, wherein orthogonal cross determined standard migration time indices of carbohydrates present in the first sample are calculated based on orthogonal internal standards of known composition.

10. The method according to claim 8, wherein the first sample is an extraction of glycans and the method allows for the identification of a glycosylation pattern profile.

11. The method according to claim 10 wherein the glycosylation pattern of a glycoprotein is identified.

12. The method according to claim 8, wherein the fluorescent label is 8-amino-1,3,6-pyrenetrisulfonic acid.

13. The method according to claim 8, wherein the method allows for high throughput identification of carbohydrate mixtures having unknown compositions.

14. The method according to claim 8, wherein carbohydrates in the first sample are determined quantitatively.

15. A method for an automated determination and/or identification of carbohydrates and/or carbohydrate mixture composition pattern profiling comprising the steps of:
- a) obtaining a sample containing one or more carbohydrate (s);
- b) labeling said one or more carbohydrate(s) with a fluorescent label;
- c) adding at least one standard of known composition to the sample containing the one or more carbohydrate(s);
- d) determining migration time(s) of said one or more carbohydrate(s) and the standard of known composition using capillary gel electrophoresis-laser induced fluorescence;
- e) normalizing the migration time(s) to migration time indice(s) based on given standard migration time indice(s) of the standard;
- f) comparing said migration time indice(s) of the one or more carbohydrate(s) with standard migration time indice(s) from a database; and
- g) identifying or determining the one or more carbohydrate (s) and/or carbohydrate mixture composition patterns, wherein the standard of known composition is a known carbohydrate mixture composition.

16. The method according to claim 1, wherein the method allows for high throughput identification of carbohydrate mixtures having unknown compositions.

17. The method according to claim 1, wherein the one or more carbohydrate(s) is determined quantitatively.

18. A system for determining and/or identifying carbohydrate mixture composition patterns, comprising:
- a data processing unit having a non-transient memory, said memory containing a database, said database containing normalized migration times and or normalized migration time indices of carbohydrates, said migration times and/or migration time indices are obtained by:
  - a) analysing known carbohydrate structure(s) in a sample together with an internal standard at the same time with a capillary gel electrophoresis-laser induced fluorescents means;
  - b) determining the migration time(s) of said carbohydrate compound(s) and the internal standard;
  - c) normalizing the migration time(s) of step b.) based on given migration time(s) of the internal standard;
  - d) assigning the normalized carbohydrate compound(s) migration time(s) to standard migration time indices whereby the normalized migration times are orthogonal cross normalized migration times and indices and where orthogonal internal standards are used; and an output unit.

19. System for determining and/or identifying carbohydrate mixture compositions and/or carbohydrate mixture composition pattern profiling comprising
- a capillary gel electrophoresis-laser induced fluorescence apparatus;
- a data processing unit comprising memory containing a database containing normalized migration times and or normalized migration time indices of carbohydrates, said migration times and/or migration time indices are obtained by:
  - a) analysing known carbohydrate structure(s) in a sample together with an internal standard at the same time with a capillary gel electrophoresis-laser induced fluorescents means;
  - b) determining the migration time(s) of said carbohydrate compound(s) and the internal standard;
  - c) normalizing the migration time(s) of step b.) based on given migration time(s) of the internal standard;
  - d) assigning the normalized carbohydrate compound(s) migration time(s) to standard migration time indices, whereby the normalized migration times are orthogonal cross normalized migration times and indices and where orthogonal internal standards are used; and an output unit.

20. A system according to claim 19, wherein the capillary gel electrophoresis-laser induced fluorescence apparatus is a capillary DNA-sequencer.

\* \* \* \* \*